US009515157B2

(12) United States Patent
Woerdenweber

(10) Patent No.: US 9,515,157 B2
(45) Date of Patent: Dec. 6, 2016

(54) SENSOR ARRANGEMENT COMPRISING A CARRIER SUBSTRATE AND A FERROELECTRIC LAYER AND METHOD FOR PRODUCING AND USING THE SENSOR ARRANGEMENT

(71) Applicant: FORSCHUNGSZENTRUM JUELICH GMBH, Juelich (DE)

(72) Inventor: Roger Woerdenweber, Niederzler (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 14/384,304

(22) PCT Filed: Mar. 9, 2013

(86) PCT No.: PCT/DE2013/000134
§ 371 (c)(1),
(2) Date: Sep. 10, 2014

(87) PCT Pub. No.: WO2013/135226
PCT Pub. Date: Sep. 19, 2013

(65) Prior Publication Data
US 2015/0068316 A1  Mar. 12, 2015

(30) Foreign Application Priority Data
Mar. 5, 2012 (DE) .......... 10 2012 005 262

(51) Int. Cl.
*G01B 7/16* (2006.01)
*H01L 29/51* (2006.01)
(Continued)

(52) U.S. Cl.
CPC .......... *H01L 29/516* (2013.01); *G01L 1/12* (2013.01); *G01L 9/0072* (2013.01);
(Continued)

(58) Field of Classification Search
CPC .......... G01J 5/34; G01J 5/20; H01L 37/02; G01L 1/12; G01L 9/0072
USPC ............ 73/760, 777, 779, 862, 391, 780
See application file for complete search history.

(56) References Cited

U.S. PATENT DOCUMENTS 4,250,384 A    2/1981  Pulvari
4,782,227 A *  11/1988 Micheron ....... H01L 27/14665
                                              250/214.1

(Continued)

FOREIGN PATENT DOCUMENTS

| EP | 0 661 754 | 7/1995 |
|---|---|---|
| JP | 2001-083176 A | 3/2001 |
| JP | 2005-347364 A | 12/2005 |

OTHER PUBLICATIONS

Improved ferroelectricity of strained SrTio3 thin films on sapphire R. Woerdenweber—E. Hollmann—R. Ott—T. Huertgen—Tai Keong Lee Springer Science * Business Media, LLC 2007 pp. 363-368.

(Continued)

*Primary Examiner* — Max Noori
(74) *Attorney, Agent, or Firm* — Norris McLaughlin & Marcus, P.A.

(57) ABSTRACT

A sensor arrangement comprises a carrier substrate and a ferroelectric layer disposed on the carrier substrate, wherein the sensor arrangement comprises means for reading the permittivity of the ferroelectric layer. The sensor arrangement is such that the ferroelectric layer is disposed in a crystalline manner on the carrier substrate. A method for producing the sensor arrangement and to use of the same is also disclosed.

22 Claims, 4 Drawing Sheets

(51) Int. Cl.
*H01L 41/113* (2006.01)
*G01L 9/00* (2006.01)
*G01L 1/12* (2006.01)
*G01N 3/08* (2006.01)
*G01J 5/20* (2006.01)
*G01J 5/34* (2006.01)

(52) U.S. Cl.
CPC .............. *G01L 9/0077* (2013.01); *G01N 3/08* (2013.01); *H01L 41/1132* (2013.01); *G01J 5/20* (2013.01); *G01J 5/34* (2013.01)

(56) References Cited

U.S. PATENT DOCUMENTS

| | | | |
|---|---|---|---|
| 5,589,725 A | 12/1996 | Haertling | |
| 5,914,507 A | 6/1999 | Polla et al. | |
| 5,938,612 A * | 8/1999 | Kline-Schoder | B06B 1/064 310/334 |
| 6,156,623 A | 12/2000 | Hendrix et al. | |
| 6,532,824 B1 | 3/2003 | Ueno et al. | |
| 7,808,236 B1 | 10/2010 | Huang et al. | |
| 8,280,210 B2 * | 10/2012 | Chowdhury | G02F 1/0009 333/239 |
| 2007/0069264 A1 * | 3/2007 | Subramanyam | H01L 29/516 257/295 |
| 2011/0147723 A1 * | 6/2011 | Hodges, Jr. | H01L 51/0529 257/40 |

OTHER PUBLICATIONS

Ferroelectric Sensors Dragan Damjanovic, Paul Muralt, and Neza Setter IEEE Sensors Journal, vol. 1, No. 3, Oct. 2001 pp. 191-206.

\* cited by examiner a.

b.

c.

a.

b.

c.

SENSOR ARRANGEMENT COMPRISING A CARRIER SUBSTRATE AND A FERROELECTRIC LAYER AND METHOD FOR PRODUCING AND USING THE SENSOR ARRANGEMENT

BACKGROUND OF THE INVENTION

The invention relates to a sensor arrangement comprising a carrier substrate and a ferroelectric layer, to a method for producing the sensor arrangement, and to the use of the sensor arrangement.

It is known that polarization Pi ($Asm^{-2}$) can be induced in an insulating, polarizable material, referred to as a dielectric, by way of an external electric field E ($Vm^{-1}$). Among dielectrics, a displacement of the charge, and thus electrical polarization of the material, is brought about in piezoelectric materials not only by external electric fields, but also by an external mechanical deformation caused by pressure, tension or torsion. The positive and negative lattice components are displaced as a result of the deformation so that an electric dipole moment is created, whereby apparent charges are induced on the surface of the outwardly neutral crystal. The term pyroelectricity collectively refers to those materials among piezoelectrics that have electric dipole moments even in the absence of an external electric field, which are caused based on distortions in the crystal lattice and the attendant displacement of charge centroids, thus bringing about electric polarization of the crystal. These substances are thus spontaneously polarized even without an electric field. Finally, the term ferroelectricity collectively refers to those substances having an electric dipole moment which change the direction of spontaneous polarization when an external electric field is applied. This phenomenon disappears above the material-dependent Curie temperature, and the material transitions into the paraelectric state. This transition is reversible, which is to say a phase transition with a structural change takes place when a drop below the Curie temperature occurs, and the material again transitions into the ferroelectric state. Permittivity, which is to say also the change in permittivity with the temperature, is typically the greatest in the range of the transition. A reversible change in permittivity which is as great as possible is thus achieved in the temperature range directly above the phase transition.

The majority of ferroelectrics are oxides. The best-known ferroelectrics are ion crystals having a perovskite structure, such as $BaTiO_3$. Some materials exhibit ferroelectric properties only in thin layers, for example $SrTiO_3$. Ferroelectric layers are essentially used in integrated circuits and in mobile radio communication technology.

It is known from more recent developments on ferroelectrics (R. Wördenweber, E. Hollmann, R. Ott, T. Hürtgen, Kai Keong Lee (2009). Improved ferroelectricity of strained $SrTiO_3$ thin films on sapphire. J Electroceram 22:363-368) to strain thin films made of ferroelectric $SrTiO_3$ (STO) by way of epitaxial growth and application of the lattice parameters on $CeO^2$ buffered sapphire, for example. The dielectric properties of the strained STO were ascertained by a capacitor on the layer.

The operating principle of pressure and bending sensors is typically based on the conversion of the parameter to be measured into an electrical signal. This can take place directly or indirectly. Pressure and bending sensors can be used to directly measure pressure or deflection and to indirectly determine other parameters, such as the temperature, the flow or the position.

Depending on the use, the desired measuring accuracy and costs, (piezo)resistive sensors, piezoelectric sensors, inductive sensors, capacitive sensors and optical sensors are employed, for example. Often, combinations of these sensors are employed, such as in a Golay cell.

A piezoelectric pressure sensor is characterized in that a charge separation is induced in the crystal having polar axes by way of the pressure to be measured, and the charge separation induces an electric voltage. This state, also known as piezoelectric effect, thus causes ions to be displaced due to pressure in the interior of the crystal, forming an electric charge on the surface that is proportional to the mechanically exerted force. The charge is converted into electric voltage proportional thereto, such as by way of an amplifier. With piezoresistive sensors, in contrast, the resistivity of the materials changes as long as they are subjected to a tensile load or pressure load. This effect also occurs in crystals without a polar axis, for example in semiconductors, such as silicon.

A general problem encountered with piezoelectric pressure sensors and the piezoresistive sensor arrangements used in strain gauges is that these have a comparatively complex design and are therefore costly. The sensitivity of these sensors likewise has some room for improvement.

Another drawback is that pyroelectricity often causes interfering artifacts in the technologically relevant field of application, which are superimposed on the piezoelectric effects that are actually of interest. Pressure sensors made of pyroelectric materials can indicate false positive signals since signals occur under heating, while no change in pressure is present at all.

SUMMARY OF THE INVENTION

It is the object of the invention to provide a sensor arrangement that has increased sensitivity over piezoelectric and pyroelectric sensors from the prior art, while being particularly easy and cost-effective to produce.

It is a further object of the invention to provide a method for producing the sensor arrangement, and use thereof.

The sensor arrangement comprises a carrier substrate and a layer disposed on the carrier substrate. The ferroelectric layer can be disposed on the entire surface of the carrier substrate, or it can be supported by the carrier substrate only at the edge. A capacitor assembly can be disposed on the ferroelectric layer as a means for reading the permittivity of the ferroelectric layer. This assembly is used to read the electrical properties of the layer based on an overpressure or underpressure that is normally exerted on the ferroelectric layer.

As an alternative, the electronic properties can be read in a non-contact manner by way of optical measurements, such as by way of ellipsometry. In this case it is possible for the ferroelectric layer to be supported by the carrier substrate only at the edge.

The ferroelectric layer is crystalline. If the layer is disposed on the entire surface of the carrier substrate, it is important that the carrier substrate responds flexibly to a small pressure acting on the sensor arrangement, and is thus deflected. The thickness of the carrier substrate should be between 1 and 500 μm.

Pressure exerted on the sensor arrangement results in compression or an expansion of the ferroelectric layer and of the carrier substrate, resulting in a detectable change in permittivity. At room temperature, the crystal of the ferroelectric layer has a centrosymmetric orientation on the substrate, or assumes this orientation on its own, which is to say the layer is in a dielectric state. The thickness of the ferroelectric layer should be approximately 1 to 1000 nm.

The system for reading permittivity detects mechanical pressure acting normally on the ferroelectric layer by way of a change in the polarizability of the ferroelectric material, which occurs because of the transition of the layer material from the centrosymmetric lattice state to a non-centrosymmetric lattice state. Depending on the arrangement of the ferroelectric layer on the carrier substrate, and depending on the arrangement of the read-out system on the ferroelectric layer and the carrier substrate, the pressure exerted results in compression or expansion of the ferroelectric layer.

The sensor arrangement according to the invention is thus based on the change in polarizability, and thus permittivity, of the ferroelectric crystals when the crystal structure changes due to pressure application. Thus, in contrast to a piezoelectric sensor, the principle is not based on the displacement of "positive charges in relation to negative" charges, but on the polarizability of crystals. Centrosymmetric crystals, which are typically not ferroelectric and have only low permittivity, are changed into non-centrosymmetric crystals by the deformation. This leads to an extreme increase in polarizability (permittivity), extending as far as induced ferroelectricity. Changes in permittivity by more than one order of magnitude can be achieved with a change in the crystal lattice parameter of <1%. This advantageously causes the sensor arrangement to have extremely high sensitivity. The change in permittivity can now very easily be read capacitively or, in a non-contact manner, optically. The sensor arrangement reads out mechanical forces based on the changing polarizability of the ferroelectric layer. In contrast to pyroelectric material, there are virtually no false positive events.

Within the context of the invention, it was surprisingly found that polarizability of the ferroelectric layer does not only result from an epitaxially grown layer with the accompanying mechanical strain on a substrate having deviating lattice parameters. But rather, it was recognized that technologically relevant, minor pressure or tension applied to the sensor arrangement can also result in a significant change in permittivity of the ferroelectric layer.

Since, with appropriate selection of the ferroelectric layer, even fractions of a change in the lattice constant, such as $10^{-4}$%, result in a measurable change in permittivity, the object is already achieved in so much as a crystalline ferroelectric layer is provided on the carrier substrate, and the permittivity thereof is read by way of an ellipsometer, for example. The optical path of the ellipsometer is directed to the ferroelectric layer and detects the change in permittivity.

As mentioned, the ferroelectric layer can be deposited onto a thin membrane as the carrier substrate. Pressures in the Pa range can advantageously be uncovered by way of the detected change in permittivity of the ferroelectric layer. The ferroelectric layer can, of course, also be disposed on the entire surface of the carrier substrate when using an optical read-out unit, for example for reasons of stability.

In one embodiment of the invention, a flexible foil-like or film-like carrier substrate made of crystalline material, such as silicon or $Al_2O_3$, or a metal or an organic material, such as polyimide, is used as the carrier substrate. The selection of the carrier material depends on the particular application and the requirements of the sensor layer. The use of foils or films ensures a high degree of strain.

The ferroelectric material is preferably made of $CaTiO_3$, $SrTiO_3$, $KTaO_3$, $BaTiO_3$, $Pb_5GeO_{11}$, $Eu_2(MoO_4)_3$, $PbTa_2O_6$, $KNbO_3$, $SrTeO_3$, $PbTiO_3$, $SrBi_2Ta_2O_9$, $LiTaO_3$, $LiNbO_3$ or a combination thereof. A list of possible ferroelectrics of these is shown in Table 1. The respective transition temperature (Curie temperature) is indicated.

TABLE 1

Ferroelectric compounds and the transition temperatures thereof

| Compound | $T_c$ [K] |
|---|---|
| $CaTiO_3$ | (−84) |
| $SrTiO_3$ | (0-44) due to strain induced phase transition 20-40 K up to room temperature |
| $KTaO_3$ | 2.8 |
| $BaTiO_3$ | 396 (compression) |
| $Pb_5GeO_{11}$ | 451 |
| $Eu_2(MoO_4)_3$ | 453 |
| $PbTa_2O_6$ | 533 |
| $KNbO_3$ | 708 |
| $SrTeO_3$ | 758 |
| $PbTiO_3$ | 763 |
| $SrBi_2Ta_2O_9$ | 843 |
| $LiTaO_3$ | 938 |
| $LiNbO_3$ | 1483 |

Alloys made of these materials (such as $(Ca,Sr)TiO_3$ or $(Ba,Sr)TiO_3$) as well as doped oxides of this series are likewise possible candidates for creating the ferroelectric layer. This advantageously allows a layer, or even a layer system, to be selected which optimally fits the particular application.

It is particularly advantageous if a ferroelectric layer made of a material having a transition temperature lower than room temperature is disposed on the carrier substrate in such a way that pressure causes tensile stress in the direction of the crystal lattice in which the electric polarization of the crystal is measured. This advantageously causes the transition temperature in the crystal direction to be increased, which also results in an increase in permittivity at room temperature in the crystal direction. Since the permittivity increases very greatly in the range before the onset of the transition to ferroelectricity, an extremely sensitive sensor is thus advantageously created.

It is also possible to dispose a ferroelectric material having a transition temperature higher than room temperature on the carrier substrate in such a way that pressure causes compressive stress in the direction of the crystal lattice in which the electric polarization of the crystal is measured. This advantageously causes the transition temperature in the crystal direction to be reduced. By analogy, the range of extremely high pressure dependency of the permittivity in the transition region can thus again be utilized.

In this way different cases can be distinguished, which are listed in Table 2, for the arrangements of vertical and planar capacitive measuring devices on a membrane having a ferroelectric layer, on which a pressure acts on the coated side.

TABLE 2

Examples of an arrangement of a membrane having a ferroelectric layer with vertical or planar capacity read-out and pressure (D > 0) or tension (D < 0) engaging on the side coated with the ferroelectric. The change in permittivity is described for cases where the transition temperature $T_c$ of the ferroelectric, layer is below or above room temperature (RT).

| | | Vertical capacitance | Planar capacitance |
|---|---|---|---|
| $T_c$ < RT | D > 0 | ε increases significantly (very advantageous) | ε decreases |
| | D < 0 | ε decreases | ε increases significantly (very advantageous) |

TABLE 2-continued

Examples of an arrangement of a membrane having a ferroelectric layer with vertical or planar capacity read-out and pressure (D > 0) or tension (D < 0) engaging on the side coated with the ferroelectric. The change in permittivity is described for cases where the transition temperature $T_c$ of the ferroelectric layer is below or above room temperature (RT).

| | Vertical capacitance | Planar capacitance |
|---|---|---|
| $T_c$ > RT | D > 0 ϵ decreases | ϵ increases significantly (very advantageous) |
| | D < 0 ϵ increases significantly (very advantageous) | ϵ decreases |

The sensor arrangement particularly advantageously comprises a ferroelectric material having a transition temperature greater than room temperature on one side of the carrier substrate, and a ferroelectric material having a transition temperature lower than room temperature on the opposite side of the carrier substrate. This advantageously allows both pressure and tensile stresses to be detected with high sensitivity.

A method for producing the sensor arrangement according to the invention provides for a ferroelectric material to be disposed on a crystalline manner on the carrier substrate by way of physical vapor deposition (PVD), chemical vapor deposition (CVD) or other deposition methods (chemical solution deposition (CSD), electrophoretic deposition (EPD) and the like), and for at least one capacitor assembly to be disposed on the ferroelectric material, the assembly detects the mechanical force exerted by way of the change in permittivity of the mechanically deformed layer. As an alternative, the permittivity can be read in a non-contact manner, for example optically by way of ellipsometry.

The described sensor arrangements are advantageously used as pressure or bending sensors. A mechanical force is exerted on the sensor arrangement in a pressure or bending sensor. This results in a reversible change in the polarizability of the ferroelectric layer and is read in a manner corresponding to the capacitor system or in a non-contact manner. After the force subsides, the polarizability of the ferroelectric layer is returned to the starting condition again.

The sensors according to the invention can be used particularly advantageously in the following fields of application:

As bending and strain sensors having extremely high sensitivity, for measuring the absolute value of bending or expansion, and for the directional-dependent and local measurement of bending or expansion with simple electronic read-out. Fields of applications include pressure measurement, overpressure control or (through-)flow measurements of gases or liquids; position determination and positioners, in touchscreens, for analog measuring transducers (such as temperature measurement in a Golay cell), and as switches, for example for triggering safety systems such as airbags, all the way to intelligent circuits.

BRIEF DESCRIPTION OF THE DRAWINGS

Identical reference numerals in the figures denote identical components.

DETAILED DESCRIPTION OF THE PREFERRED EMBODIMENTS

Figure 1:
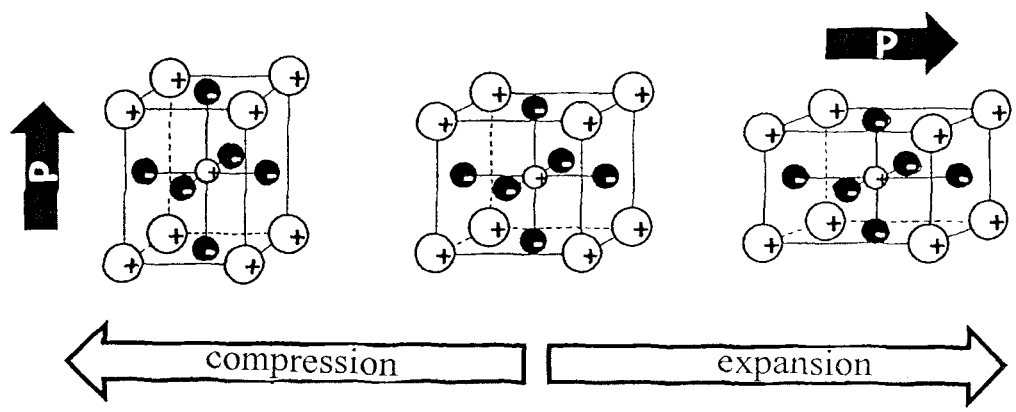
FIG. 1: shows a principle of the sensor arrangement according to the invention.
Figure 1:
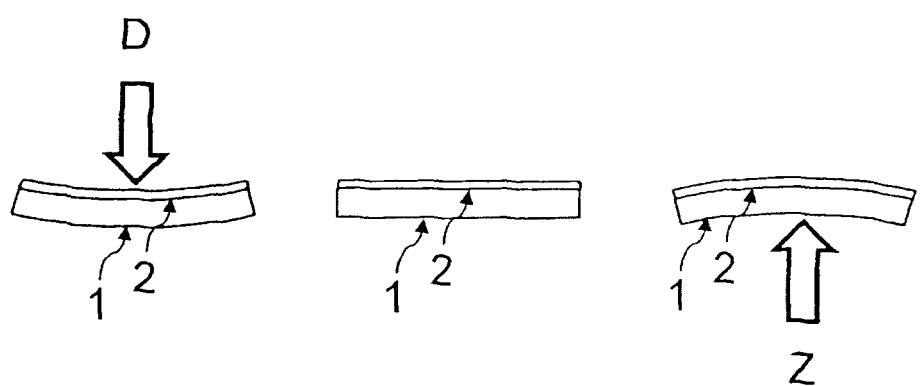

FIG. 1 shows the principle of the sensor arrangement according to the invention. Polarizability is a measure of the displaceability of a positive charge relative to a negative charge when an external electric field is applied. The higher the polarizability is, the more easily a dipole moment can be induced by an electric field. Polarizability is composed of an electric portion (displacement of the electron cloud relative to the nuclei) and an ionic portion (displacement of positive ions relative to negative ions). Ionic polarizability provides the greatest contribution to permittivity. Moreover, the ionic contribution is highly dependent on the crystal structure, in particular on crystal symmetry. It generally holds true that centrosymmetric crystals cannot be ferroelectric (FIG. 1, center).

According to the invention, the crystal structure, and also the crystal symmetry, is changed by (uniaxial or biaxial) pressure, see FIG. 1, left and right. This brings about a change in the polarizability P of the crystals. According to the invention, the greatest change is to be expected when a non-centrosymmetric structure (left and right) is created from a centrosymmetric structure (center). Here, a ferroelectric state is created from a dielectric state by lattice distortion. This causes enormous changes in permittivity. In the case of epitaxial, monocrystalline layers, the inventor measured an increase from ϵ≈300 to ϵ≈5000 in a perovskite ($ABO_3$ structure) with a change in the lattice constant of only approximately 1%. It is the inventive assumption of the invention that similar modifications in permittivity can also be achieved mechanically with pressure changes in the Pa range. The bottom portion of the figure in each case shows an arrangement of the layer on the carrier for the different states. The ferroelectric layer 2 is disposed on the carrier substrate 1. The thick arrows on the left and right at the bottom of FIG. 1 indicate the overpressure D (left) and underpressure D (right) acting on the arrangement. Depending on the arrangement of the ferroelectric layer, this results in compression or expansion of the crystal structure in the layer plane. This compression or expansion is then partially compensated for by the opposite expansion or compression perpendicular to the layer plane. The effect can take place in an exactly reversed manner by additionally arranging the layer under the carrier.

It generally holds true that a positive or negative pressure normal to the membrane causes a compression or expansion in the layer plane of the ferroelectric layer, with simultaneous compensation normal to the layer plane.

P in the upper portion of FIG. 1 indicates the direction of polarizability of the crystal when, as is shown in the bottom portion, an overpressure or underpressure acts on the ferroelectric layer.

Figure 2:
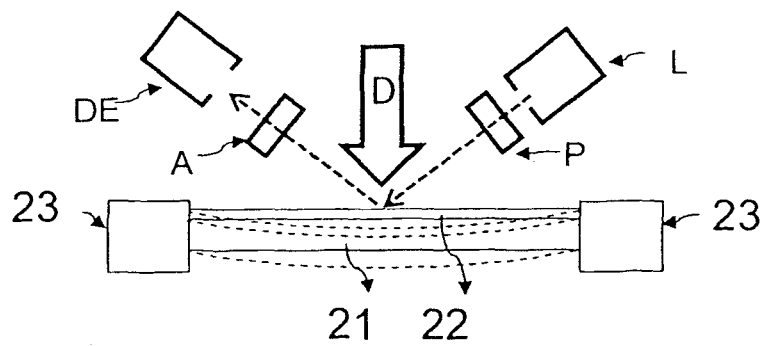
FIG. 2: shows a schematic illustration (sectional view) of sensor arrangements according to the invention comprising a carrier substrate and a ferroelectric layer with optical reading.
Figure 2:
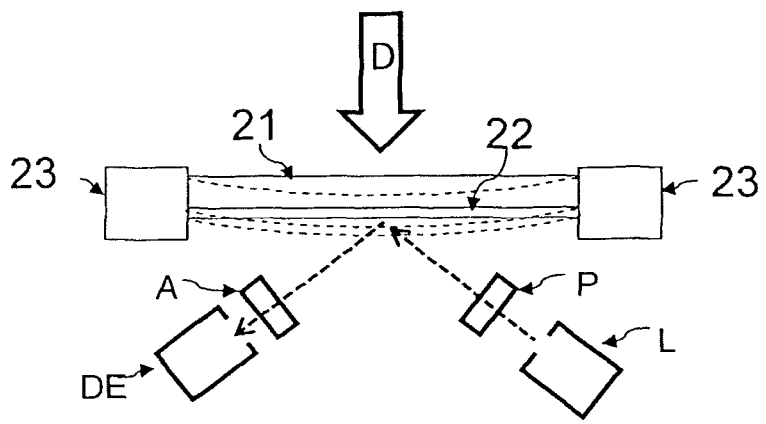
Figure 2:
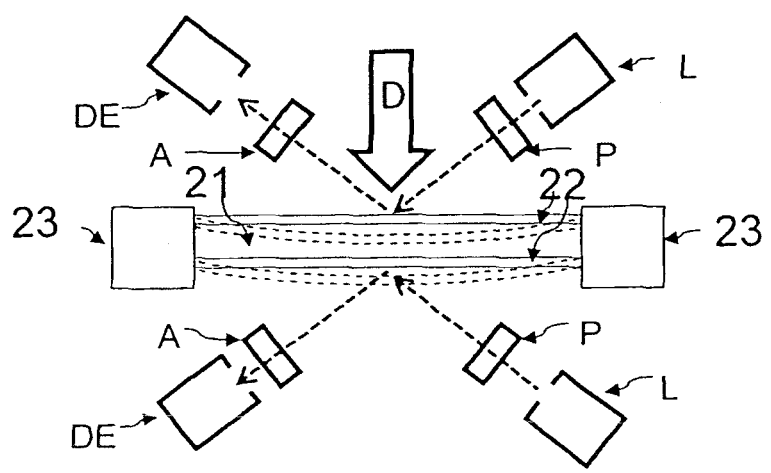

FIG. 2 shows the pressure sensor with optical reading (ellipsometry), consisting of a light source L, polarizer P, analyzer A and detector DE. The following cases are shown:

a) Ferroelectric layer on the side of the membrane facing the pressure (D>0). Alternatively the membrane can be dispensed with, and the ferroelectric layer can be designed as the membrane.
b) Ferroelectric layer under the side of the membrane facing the pressure (D>0). Alternatively the membrane can be dispensed with, and the ferroelectric layer can be designed as the membrane.
c) Membrane coated on both sides with a ferroelectric sensor layer is read optically on both sides. Alternatively the membrane can be dispensed with, and the ferroelectric layer can be designed as the membrane.

The dotted lines in the figures for the membrane 21 and for the detector layer 22 indicate the states of the same deflected from the neutral position after pressure load D.

The figures schematically show the basic elements of the pressure or tensile sensor with optical reading, comprising the membrane holder 23 of the membrane 21 and the sensor layer 22. The dotted line indicates the deflected state of the membrane with the sensor layer based on a pressure D. The dotted arrows describe the optical beam for optical reading, such as by way of ellipsometry. For microscopic measurements, the membrane can have lateral dimensions of several micrometers to several centimeters for non-spatially-resolved highly sensitive measurements. The thickness of the membrane 21 can be selected in the range of 10 μm. The thickness of the sensor layer is typically 200 nm. Here, it is also conceivable to operate without the carrier substrate 21, for example when using a sufficiently thick sensor layer (2 μm), the deflection of which causes the top side and bottom side of the crystal structure to be strained opposite from each other and only one of the two surfaces to be captured by the optical reading.

Figure 3:
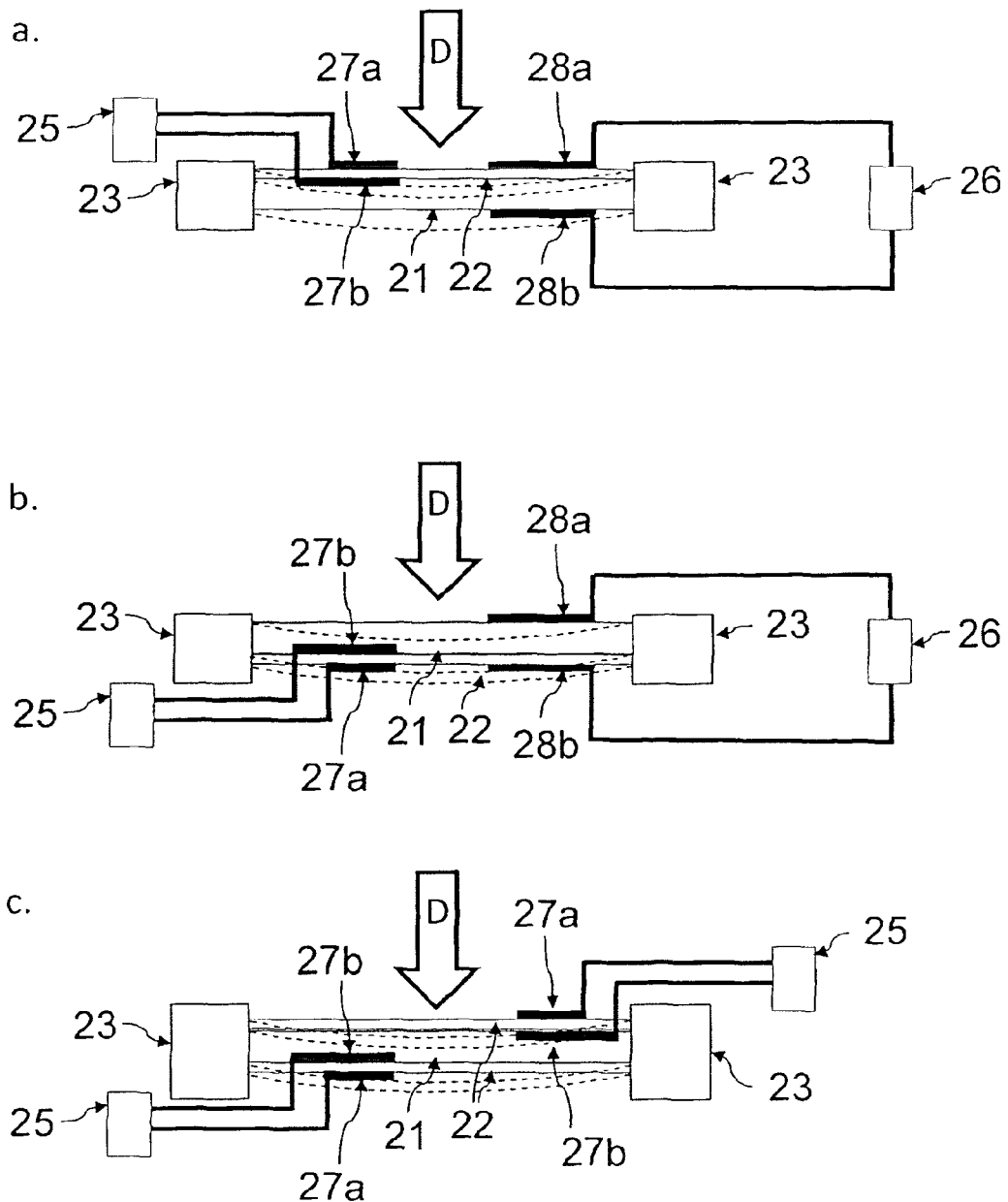
FIG. 3: shows a schematic illustration (sectional view) of sensor arrangements according to the invention comprising a carrier substrate and a ferroelectric layer with capacitive reading.

FIG. 3 shows the pressure sensor with capacitive reading by way of a plate capacitor assembly for determining the normal polarization of the ferroelectric layer. The plate capacitor comprises electrodes 27 and 28 and the electronically connected reading electronics 26. The following cases are shown:
a) Ferroelectric layer on the side of the membrane facing the pressure (D>0), comprising an electrode pair 27 including only the ferroelectric layer, and an electrode pair 28 including the ferroelectric layer and the membrane.
b) Ferroelectric layer under the side of the membrane facing the pressure (D>0), comprising an electrode pair 27 including only the ferroelectric layer, and an electrode pair 28 including the ferroelectric layer and the membrane.
c) Double-sided reading of a membrane coated on both sides with ferroelectric sensor layers by way of two electrode pairs 27a, 27b including only the ferroelectric layer, wherein one electrode pair measures on the top layer, while the second electrode pair measures on the bottom layer.

FIG. 3 shows a schematic illustration of the sensor arrangement in a sectional view, composed of a carrier, which here is a membrane 21 for pressure measurements, a ferroelectric perovskite layer 22 serving as the detector layer, an annular holder 23 serving as the carrier substrate for the layers 21, 22, as in FIG. 2, however with capacitive reading electrodes 27a, 27b, 28a, 28b and capacitive reading electronics 25, 26.

The change in permittivity can thus also be read capacitively, as is shown in the figures. A parallel plate capacitor assembly can be selected for this purpose. The polarizability of the detector layer 22 is determined normal to the carrier substrate 21 or to the membrane plane.

Arrow D, in turn, indicates the pressure on the carrier substrate 21 and the detector layer 22. A parallel plate capacitor 27a, 27b is shown to the left of arrow D, in which the electrodes include only the detector layer; to the right thereof a parallel plate capacitor 28a, 28b is shown, in which the two electrodes comprise the membrane or carrier substrate 21 and the sensor layer as the ferroelectric layer 22. Since the dielectric properties of the carrier substrate and of the ferroelectric sensor layer are measured, in this case on the right, it must be ensured here that the permittivity, and more particularly the change in permittivity during deflection, is negligibly small. Both structures are possible in combination, as shown, or individually.

The parallel plates 27a, 27b and 28a, 28b form the capacitances C:

$$C = \varepsilon_o \varepsilon \frac{A}{d}, \qquad \text{(equation 1)}$$

wherein $\varepsilon_0 = 8.85 \cdot 10^{-12}$ [As/Vm] denotes the electric field constant, $\varepsilon$ denotes the dielectric constant or permittivity of the medium between the plates, and A and d denote the surface and distance of the plates, respectively. Thus, in general the following applies to these arrangements and to the planar arrangements of the electrodes on the detector layer:

$$C \propto \varepsilon. \qquad \text{(equation 2)},$$

The higher sensitivities are essentially achieved by extending the effective gap using interdigital structures 30a, 30b.

Figure 4:
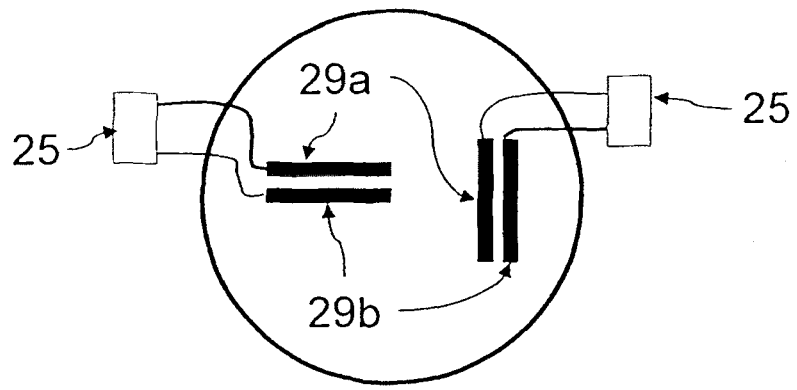
FIGS. 4a, b: show top views of different capacitive reading capacitors.
Figure 4:
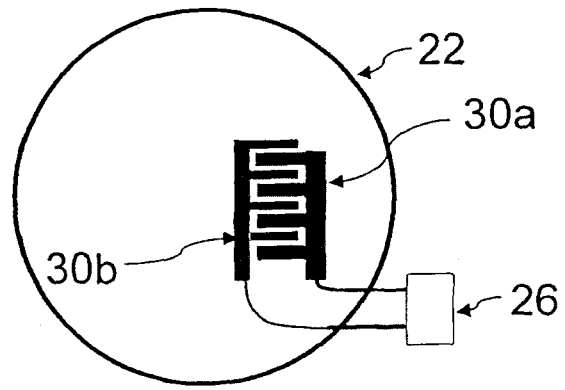
Figure 4:
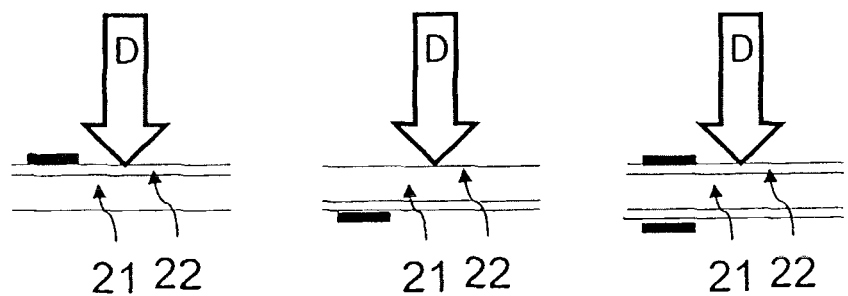

FIG. 4 shows top views (in (a) and (b)) of different capacitive reading capacitors for determining the planar polarizability, which is to say the permittivity in the layer plane. The electrode pairs are applied to the ferroelectric sensor layer in each case. Again, the membrane serving as the carrier can be dispensed with.
a) Planar parallel plate assembly in standard design.
b) Planar interdigital structure, with which higher resolutions on smaller measuring surfaces are achieved.
c) Different measuring arrangements in a transverse view show the possible positioning of the planar electrode pairs.
From the left:
A planar electrode pair is disposed on the ferroelectric layer, which in turn is disposed on the membrane, and determines the planar expansion/compression of the ferroelectric layer below the membrane.

A planar electrode pair is disposed under the ferroelectric layer, which in turn is disposed under the membrane, and determines the planar expansion/compression of the ferroelectric layer above the membrane. Here, the expansion and compression in the layers above and below the membrane can be determined simultaneously.

Planar structures are advantageously used to measure the permittivity of the detector layer 22 in the layer plane. Depending on the goal of the application, different capacitor structures can thus be used, such as standard structures composed of two strips 29a, 29b disposed in parallel, at a minimal distance, or interdigital structures 30a, 30b having increased capacitance. Here, the permittivity, and thus the deflection in different directions, can be determined separately by way of the orientation of the capacitor structures. The planar arrangements determine the permittivity only in the direction that is predefined by the electrodes. This arrangement is thus suited for measuring the deflection of the membrane with the sensor layer in a direction predefined by the electrode structure. In this arrangement, the sensor thus also functions as a deflection sensor. Due to the different arrangement of the capacitor structures, the deflection of the membrane with the sensor layer can now be evidenced in different directions.

In general, the local change in deflection can be determined by miniaturization of the capacitor structures. Moreover, dynamic locally resolved processes can be captured (for example, for touchscreens) by way of temporal data acquisition.

The sensor arrangement is produced as follows.

An Si carrier is used as the carrier material 21, in which a region is thinned to approximately 2 to 5 µm by way of etching, so that a thin, flexible membrane is created on a round surface measuring approximately 10 mm in diameter. The wafer is now provided with a thin crystalline ferroelectric layer made of $SrTiO_3$ on the planar side by way of magnetron cathode sputtering. The layer thickness of the $SrTiO_3$ layer is approximately 50 nm. An electrode pair, including feed lines for the capacitive measurement, is now applied to this layer using thin-film technology by way of a lift-off method and gold evaporation. The electrodes for the capacitive measurement of the permittivity are located on the membrane, and the feed lines from the electrodes lead to contacts of the measuring electronics 25, 26 outside the membrane. The electrodes are composed of rectangles measuring 8 mm×1 mm, the long edges of which are disposed parallel to each other and form a gap of 2 µm.

The Si wafer is applied to a Golay cell in a vacuum-tight manner. Using the feed lines located outside the membrane, the capacitance of the capacitive system on the membrane is now determined by way of an LC meter. Changes in the temperature of the Golay cell cause a pressure change in the interior of the cell, leading to a deflection of the Si membrane 21. The change in permittivity of $SrTiO_3$ effected by the deflection of the membrane now causes a change in capacitance. The change in the temperature of the Golay cell is thus converted into an easy-to-measure change in capacitance.

A deflection of the carrier layer 21 and of the detector layer 22 due to a pressure change D thus always affects the capacitor assembly 27a, 27b, including the measuring electronics 25 and 28a, 28b and 26, as well as 29a, 29b and 30a, 30b. Capacitances from the pF range to the µF range can thus be read this way.

The invention claimed is:
1. A sensor arrangement comprising:
  a carrier substrate;
  a ferroelectric layer disposed in a crystalline manner on the carrier substrate and forming a crystalline lattice, the ferroelectric layer disposed relative to the carrier substrate in a configuration by which mechanical distortion of the carrier substrate causes a mechanical distortion of the crystalline lattice and a change in polarizability of crystals among the crystalline lattice, wherein said change in polarizability of the crystals is accompanied by a change in permittivity of the ferroelectric layer;
  a plurality of planar plates configured relative to the ferroelectric layer to form one or more capacitive reading capacitors having a capacitance that is proportional to said permittivity of the ferroelectric layer, a first one capacitor of said one or more capacitive reading capacitors comprising a first planar electrode extending over a region of the ferroelectric layer that is less than an entire face of the ferroelectric layer.
2. The sensor arrangement according to claim 1, wherein the carrier substrate is a flexible carrier substrate.

3. A sensor arrangement according to claim 1, wherein the carrier substrate comprises silicon or $Al_2O_3$ or polyimide or a metal.

4. The sensor arrangement according to claim 1, comprising a ferroelectric material made of $CaTiO_3$, $SrTiO_3$, $KTaO_3$, $BaTiO_3$, $PbsGeO_{11}$, $Eu_2(MoO_4)_3$, $PbTa_2O_6$, $KNbO_3$, $SrTeO_3$, $PbTiO_3$, $SrBi_2Ta_2O_9$, $LiTaO_3$, $LiNbO_3$ or a combination of these materials.

5. A sensor arrangement according claim 1, wherein the ferroelectric layer comprises a material having a transition temperature lower than room temperature, so that a pressure results in tensile stress on the crystal lattice of the ferroelectric layer.

6. A sensor arrangement according claim 1, comprising a ferroelectric material having a transition temperature higher than room temperature is disposed on the carrier substrate, so that a pressure results in compressive stress on the crystal lattice.

7. A sensor arrangement according to claim 1, comprising a ferroelectric material having a transition temperature higher than room temperature and being disposed on one side of the carrier substrate, and a ferroelectric material having a transition temperature lower than room temperature and being disposed on the opposite side of the carrier substrate.

8. A method for producing a sensor arrangement according to claim 1, comprising disposing a ferroelectric material in a crystalline manner on the carrier substrate by way of physical vapor deposition, chemical vapor deposition, chemical solution deposition or electrophoretic deposition.

9. A method of sensing with the sensor arrangement according to claim 1 configured as a pressure or bending sensor, comprising:
  receiving a mechanical force that is normally exerted on the sensor arrangement;
  undergoing in response to said mechanical force a reversible change in the polarizability of the ferroelectric layer; and
  after the force subsides, undergoing a return of the polarizability of the ferroelectric layer to the starting condition again.

10. The method of sensing according to claim 9, further comprising measuring the pressure at the transition temperature of the ferroelectric layer.

11. The sensor arrangement according to claim 1, wherein said first planar electrode is located on a first surface of the ferroeletric layer opposite the carrier substrate, and
  wherein said first one capacitor further comprises a second planar electrode located at an interface between the carrier substrate and a second face of the ferroelectric layer, said second planar electrode encompassing an area less than an entirety of said interface.

12. The sensor arrangement according to claim 1, wherein said first planar electrode is located on a first surface of the ferroeletric layer opposite the carrier substrate, and
  wherein said first one capacitor further comprises a second planar electrode located on a first surface of the carrier substrate opposite the ferroelectric layer, said second planar electrode encompassing an area less than an entirety of said first surface of the carrier substrate.

13. The sensor arrangement according to claim 11, wherein said one or more capacitive reading capacitors comprises a second capacitor comprising:
  a third planar electrode extending over a second region of first surface of the ferroelectric layer that is less than an entirety of said first surface of the ferroelectric layer, and a fourth planar electrode located on a first surface of the carrier substrate opposite the interface, said second planar electrode encompassing an area less than an entirety of said first surface of the carrier substrate.

14. The sensor arrangement according to claim 1, wherein the plurality of planar plates are configured relative to the ferroelectric layer to form a plurality of said capacitive reading capacitors, wherein said first capacitive reading capacitor and a second capacitive reading capacitor among said plurality of capacitive reading capacitors are configured respectively at a different orientation;
   wherein said first capacitive reading capacitor detects a corresponding first component direction of a change in polarizability of the crystals based on a measured capacitance at said first capacitive reading capacitor; and
   wherein said second capacitive reading capacitor detects a corresponding second component direction of a change in polarizability of the crystals based on a measured capacitance at said second capacitive reading capacitor.

15. The sensor arrangement according to claim 1,
   wherein the ferroelectric layer is a first ferroelectric layer disposed on one side of the carrier substrate;
   further comprising a second ferroelectric layer disposed as a crystalline structure on another side of the carrier substrate and forming a second crystalline lattice, the second ferroelectric layer disposed relative to the carrier substrate in a configuration by which mechanical distortion of the carrier substrate causes a mechanical distortion of the second crystalline lattice and a change in polarizability of crystals among the second crystalline lattice, wherein said change in polarizability of the crystals among the second crystalline lattice is accompanied by a change in permittivity of the second ferroelectric layer;
   wherein the first ferroelectric layer has a transition temperature between a dielectric state and a ferroelectric state that is less than room temperature and the second ferroelectric layer has its transition temperature between the dielectric state and the ferroelectric state that is greater than room temperature so that a measurement sensitivity of the sensor arrangement for a first direction of mechanical distortion of the carrier substrate is greater at said first ferroelectric layer than at said second ferroelectric layer, and the measurement sensitivity of the sensor arrangement for a second direction of mechanical distortion of the carrier substrate is greater at said second ferroelectric layer than at said first ferroelectric layer.

16. A sensor that detects mechanical pressure acting on a membrane, the sensor comprising:
   a carrier substrate;
   a ferroelectric layer disposed in a crystalline manner on the carrier substrate and forming a crystalline lattice, the carrier substrate and ferroelectric layer forming the membrane; and
   a plurality of planar plates configured relative to the ferroelectric layer to form one or more capacitive reading capacitors having a capacitance that is proportional to said permittivity of the ferroelectric layer,
   wherein the ferroelectric layer is disposed relative to the carrier substrate in a configuration by which mechanical distortion of the carrier substrate causes a mechanical distortion of the crystalline lattice and a change in polarizability of crystals among the crystalline lattice, wherein said change in polarizability of the crystals is accompanied by a change in permittivity of the ferroelectric layer;
   wherein a pair of planar plates among said plurality of planar plates, along with a portion of the membrane therebetween, forms a first capacitive reading capacitor, a capacitance of the first capacitive reading capacitor being a measure of said mechanical pressure, said capacitance varying according to said mechanical pressure.

17. The sensor of claim 16, wherein said pair of planar plates comprise a first planar electrode extending over a first face of the ferroelectric layer that is less than an entirety of said first face of the ferroelectric layer, and
   a second planar electrode located at an interface between the carrier substrate and a second face of the ferroelectric layer, said second planar electrode encompassing an area less than an entirety of said interface.

18. The sensor of claim 16, wherein said pair of planar plates comprise a first planar electrode extending over a first face of the ferroelectric layer that is less than an entirety of said first face of the ferroelectric layer; and
   a second planar electrode located on a first surface of the carrier substrate opposite the ferroelectric layer, said second planar electrode encompassing an area less than an entirety of said first surface of the carrier substrate.

19. The sensor of claim 16, wherein said plurality of planar plates comprises a second pair of planar plates configured relative to the ferroelectric layer to form a second capacitive reading capacitor, wherein said first capacitive reading capacitor and said second capacitive reading capacitor are configured to have a differing orientation;
   wherein said first capacitive reading capacitor detects a corresponding first component direction of a change in polarizability of the crystals based on a measured capacitance at said first capacitive reading capacitor; and
   wherein said second capacitive reading capacitor detects a corresponding second component direction of the change in polarizability of the crystals based on a measured capacitance at said second capacitive reading capacitor.

20. The sensor of claim 16, wherein the ferroelectric layer is a first ferroelectric layer disposed on one surface of the carrier substrate;
   further comprising a second ferroelectric layer disposed as a crystalline structure on another surface of the carrier substrate and forming a second crystalline lattice, the second ferroelectric layer disposed relative to the carrier substrate in a configuration by which mechanical distortion of the carrier substrate causes a mechanical distortion of the second crystalline lattice and a change in polarizability of crystals among the second crystalline lattice, wherein said change in polarizability of the crystals among the second crystalline lattice is accompanied by a change in permittivity of the second ferroelectric layer;
   wherein the first ferroelectric layer has a transition temperature between a dielectric state and a ferroelectric state that is less than room temperature and the second ferroelectric layer has its transition temperature between the dielectric state and the ferroelectric state that is greater than room temperature, so that sensitivity of said measure of mechanical pressure for a first direction of mechanical distortion of the carrier substrate is greater at said first ferroelectric layer than at said second ferroelectric layer, and sensitivity of said measure of mechanical pressure for a second direction of mechanical distortion of the carrier substrate is greater at said second ferroelectric layer than at said first ferroelectric layer.

21. The sensor of claim 16, wherein the carrier substrate comprises silicon or $Al_2O_3$ or polyimide or a metal.

22. The sensor of claim 16, wherein the ferroelectric layer comprises a ferroelectric material made of $CaTiO_3$, $SrTiO_3$, $KTaO_3$, $BaTiO_3$, $PbsGeO_{11}$, $Eu_2(MoO_4)_3$, $PbTa_2O_6$, $KNbO_3$, $SrTeO_3$, $PbTiO_3$, $SrBi_2Ta_2O_9$, $LiTaO_3$, $LiNbO_3$ or a combination of these materials.

* * * * *